US011998067B2

(12) United States Patent
Jeandupeux

(10) Patent No.: US 11,998,067 B2
(45) Date of Patent: Jun. 4, 2024

(54) AIRBAG SAFETY DEVICE

(71) Applicant: SERVICE A LA PERSONNE TECHNOLOGIE ACTIVE SARL, Châtelaine (CH)

(72) Inventor: Thierry Jeandupeux, Dingy en Vuache (FR)

(73) Assignee: SERVICE A LA PERSONNE TECHNOLOGIE ACTIVE SARL (CH)

( * ) Notice: Subject to any disclaimer, the term of this patent is extended or adjusted under 35 U.S.C. 154(b) by 837 days.

(21) Appl. No.: 17/050,464

(22) PCT Filed: Apr. 23, 2019

(86) PCT No.: PCT/IB2019/053333
§ 371 (c)(1),
(2) Date: Oct. 26, 2020

(87) PCT Pub. No.: WO2019/207474
PCT Pub. Date: Oct. 31, 2019

(65) Prior Publication Data
US 2021/0235787 A1 Aug. 5, 2021

(30) Foreign Application Priority Data

Apr. 26, 2018 (CH) ..................................... 00536/18
May 11, 2018 (CH) ..................................... 00588/18

(51) Int. Cl.
*G08B 21/04* (2006.01)
*A41D 13/018* (2006.01)
(Continued)

(52) U.S. Cl.
CPC ....... *A41D 13/018* (2013.01); *A41D 13/0506* (2013.01); *A61B 5/1117* (2013.01);
(Continued)

(58) Field of Classification Search
CPC ....................... A41D 13/018; A41D 13/0506; A61B 5/1117; A61B 5/6823; A61B 5/103;
(Continued)

(56) References Cited

U.S. PATENT DOCUMENTS 6,139,050 A * 10/2000 Bultel .................. A41D 13/018
280/730.1
6,828,697 B2 * 12/2004 Mattes ................. A41D 13/018
307/116
(Continued)

FOREIGN PATENT DOCUMENTS

WO WO 2017/151645 9/2017
WO WO-2017151645 A1 * 9/2017 ........... A41D 13/018

*Primary Examiner* — Jessica L Laux
*Assistant Examiner* — Kathleen M. McFarland

(57) ABSTRACT

A safety device adapted to be worn by a wearer (6) for preventing the injuries in particular to the hips by airbag inflation, comprises: a portable inflatable bag (1); a source (2) of releasable gas coupled to the bag (1); a belt buckle (3, 4) in which a plurality of sensors are arranged, one of which measures the ambient temperature and the other thermal sensor (5) measures the body temperature of a wearer (6) to enable triggering of the airbag in case of a fall only when the device is worn by a wearer.

10 Claims, 5 Drawing Sheets

(51) Int. Cl.
*A41D 13/05* (2006.01)
*A61B 5/00* (2006.01)
*A61B 5/103* (2006.01)
*A61B 5/11* (2006.01)
*H04W 4/30* (2018.01)

(52) U.S. Cl.
CPC ........ *A61B 5/6823* (2013.01); *G08B 21/0446* (2013.01); *H04W 4/30* (2018.02); *A61B 5/103* (2013.01)

(58) Field of Classification Search
CPC ....... A61B 5/01; A61B 5/1122; A61B 5/6804; G08B 21/0446; H04W 4/30; G01P 15/00
See application file for complete search history.

(56) References Cited

U.S. PATENT DOCUMENTS

| | | | |
|---|---|---|---|
| 6,859,939 B1* | 3/2005 | Osburn, Sr. | A41D 13/018 128/869 |
| 7,017,195 B2* | 3/2006 | Buckman | A61B 5/1117 2/455 |
| 7,150,048 B2* | 12/2006 | Buckman | A61B 5/6805 2/455 |
| 10,539,941 B2* | 1/2020 | Hyde | A63B 71/081 |
| 10,897,938 B2* | 1/2021 | Davenport | A41D 1/002 |
| 2005/0067816 A1 | 3/2005 | Buckman | |
| 2014/0047623 A1* | 2/2014 | Richards | A41D 13/018 2/455 |
| 2017/0208874 A1* | 7/2017 | Davenport | A41D 13/018 |
| 2017/0277158 A1* | 9/2017 | Hyde | A01K 13/006 |
| 2019/0069612 A1* | 3/2019 | Hyde | H01H 35/14 |

* cited by examiner

AIRBAG SAFETY DEVICE

The present invention relates to an airbag safety device for preventing injuries to the hips, the pelvis, the buttocks and the coccyx in case of a fall.

US2015351666A1 describes a movement analysis system including at least one orientation sensor configured to detect movement of the torso in three dimensions over time, as well as an airbag triggered during a fall in order to cushion the body of the user. This device is restrictive and uncomfortable to the extent that a plurality of sensors is distributed over the system, including a sensor disposed on the user's neck.

U.S. Pat. No. 6,920,647B2 describes a device for protecting the hip for minimizing the risk of rupture of the hip during a fall. This device has a system for detecting the rate and the degree of change in the user's attitude, thus allowing the device to be switched on during a possible fall in order to inflate bags and dampen the fall.

WO2017/151645 describes a protective device comprising an inflatable cushion assembly configured to extend at least partially around the waist or hips of an individual, a buckle fastened to the inflatable cushion assembly, the buckle comprising a first buckle half, and a second buckle half, the first and second buckle halves being attachable and detachable from each other. The device comprises an inflatable cushion actuator configured to actuate the inflatable cushion assembly. A part of the inflatable cushion actuator is disposed in the first buckle half or the second buckle half. A drawback of this implementation is that the device can be triggered unexpectedly even if it is not worn by a user around the belt but for example just carried by hand to be stored.

The aim of the present invention is to propose an airbag safety device which is not very restrictive for the user and which is not triggered unexpectedly.

The invention concerns a safety device adapted to be worn by a wearer, of the type for preventing injuries to the hips, the pelvis, the buttocks and the coccyx by airbag inflation, comprising: a portable inflatable bag, which can be coupled to a garment; at least one source of releasable gas coupled to the bag; a belt buckle in which a plurality of sensors are arranged, for determining the angular movement and the acceleration of a wearer during a fall; a microcontroller adapted to analyze the data received by different functional blocks in order to define the time for triggering the gas source; and means for releasing the gas from the source into the bag according to a determination by the microcontroller that the wearer is falling.

According to the invention, two of the sensors arranged in the buckle are a first thermal sensor measuring the ambient temperature and a second thermal sensor measuring the body temperature of a wearer. The first and second thermal sensors are arranged for triggering of the airbag in case of a fall only when the device is worn by a wearer, in particular by measuring the temperature difference measured by the two thermal sensors thus ensuring the presence of a wearer.

In one embodiment, the buckle includes at least one pair of magnets, preferably two pairs, for locking the buckle.

In another embodiment, the buckle includes a piston contact for activating the device, once the belt is closed.

In one embodiment, the device includes a rechargeable energy source through the buckle, in particular by a USB cable.

In all embodiments, the device may include a six-axis inertial module for detecting the movements of a wearer, the inertial module including in particular an accelerometer coupled to a gyroscope.

According to a particular embodiment, the buckle includes an opening arranged to pass an electric wire disposed to transmit an electrical pulse given by the microcontroller to enable triggering of the airbag in case of a fall.

In one embodiment, visual and/or sound means are arranged to indicate the operating state of said device.

Preferably, the buckle comprises (A) a first cylindrically shaped portion including a helical groove extending from one end of the first buckle portion, the groove being slightly curved with a notch at the second end thereof, and (B) a second portion including a protrusion arranged to slide in said groove and be engaged into said notch. Each portion of the buckle includes a magnet arranged to hold together the first and second buckle portions, the two said buckle portions being disengageable from each other by the angular displacement, notably by at least one eighth of a turn, of a first buckle portion relative to the other buckle portion, then by the sliding of the protrusion in the groove until it is fully extracted.

Such a buckle, provided or not with electronics, can easily be arranged on other forms of belts, in particular to facilitate the opening and closing of the buckle.

In one embodiment, the buckle is in particular formed of two assemblable portions, a first portion in the form of a rectangular housing containing electronics and a second portion which is also rectangular, these two portions together including a cylindrical connection body including a bayonet fastening device. The outer sides of said portions of this buckle include openings to be attached to the ends of the bag forming a belt.

In order to enhance the safety of the wearer, the device includes a wireless communication module, in particular by radio link, capable of transmitting information relating to the triggering of the airbag to a person other than the wearer of said device. The communication module also allows the geolocation of the wearer. The device can in particular provide, thanks to a corresponding supervision system, on the one hand, a state of the device that a third person, for example a doctor or a relative, can monitor at any time and in real time via the communication, and on the other hand, the geolocation of the wearer.

Preferably, the communication module is a low consumption module so as to minimize its power consumption.

The communication module is capable of transmitting information relating to a state of the device corresponding to the presence or absence of a wearer and the triggering or not of the airbag.

In one embodiment, the microcontroller stores an algorithm which records each movement which can be called a non-standard movement, that is to say, each movement which could correspond either to a fall or to a very sudden movement, but which is not a fall. Thus, by accurately determining a movement corresponding to a fall, the microcontroller will be able to define, in an accurate and relevant manner, the time to trigger the gas source and release the gas from the source into the bag. At regular intervals, the microcontroller therefore reloads a new improved and optimized algorithm. Preferably, this update of the software is carried out when the user connects his safety device to a computer. In a variant, the update of the software can be done remotely by a technician who would connect to the safety device.

Preferably, each time the airbag is triggered, the device is configured to send an alert signal, in particular an SMS or an emergency telephone call to alert a third party. The safety device can be connected via a wireless internet connection to an application capable of relaying alerts by SMS and/or e-mail associated with competent services. The safety device can also be connected to a cellular phone of a user that can relay alerts on the one hand, and the user's location on the other hand, by using a cellular connection and GPS coordinates.

In one embodiment, the safety device includes, on the buckle thereof, a control such as a push button configured to send an alert to a third person such as a caregiver.

In order to enhance safety, the gas source can be arranged in a bag which retains it so that it cannot be propelled in case of triggering of the airbag (additional securing).

The features of the invention will appear more clearly on reading the description of an embodiment given only by way of example, which is in no way limiting by referring to the schematic figures, in which.

Figure 1:
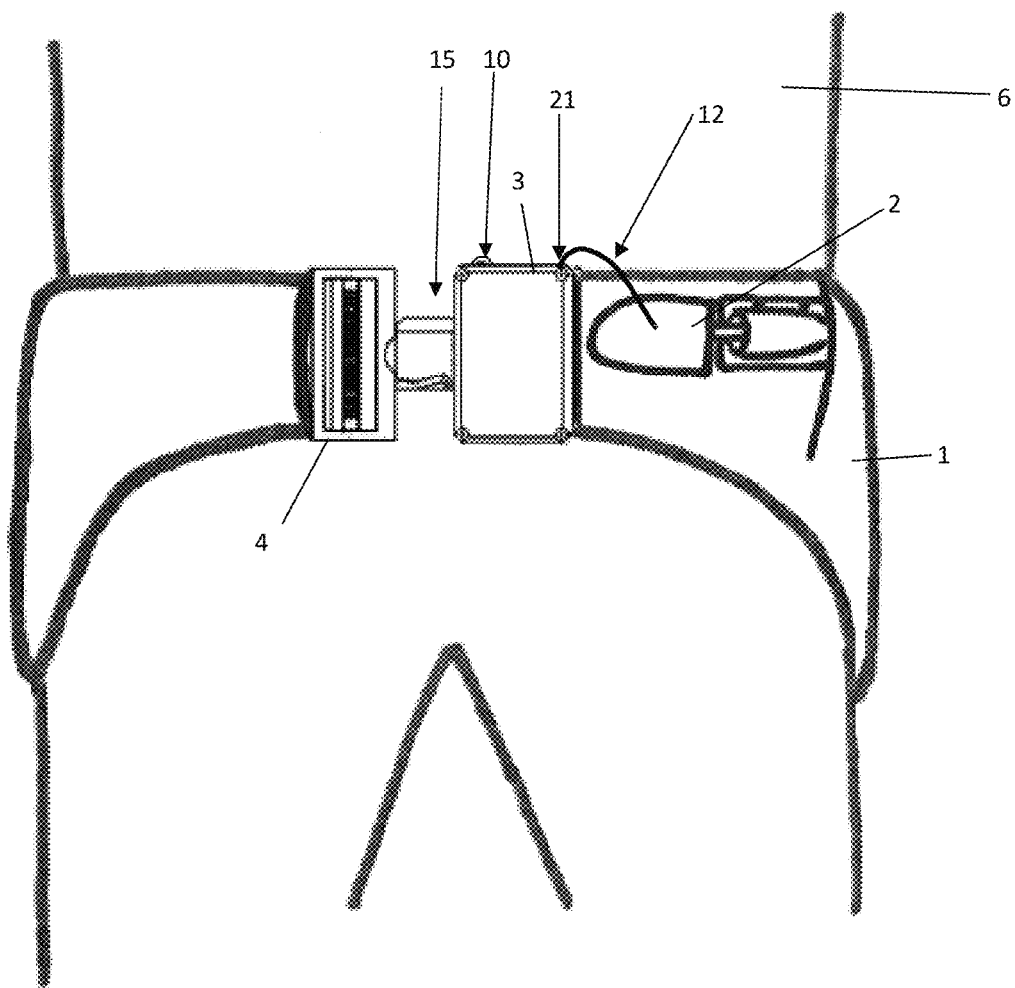
FIG. 1 is a schematic diagram showing an airbag safety device worn by a wearer.

FIG. 1 shows an airbag safety device according to the invention worn by a wearer 6 so as to prevent injuries to the hips, the pelvis, the buttocks and the coccyx by inflation of an airbag adapted to the hips of a wearer 6. This device comprises a portable inflatable bag 1 that can be coupled around a garment of the wearer 6.

The inflatable bag 1 carries a source 2 of releasable gas coupled to the bag 1. The inflatable bag 1 is carried by a belt buckle 3, 4 in which a plurality of sensors are arranged, for determining the angular movement and the acceleration of a wearer during a fall. The buckle 3, 4 also contains a microcontroller adapted to analyze data received by the different functional blocks in order to define the time to trigger the gas source 2, as well as means for releasing the gas from the source 2 to fill the bag 1 according to a determination by the microcontroller that the wearer 6 is falling. The microcontroller constitutes the heart of the apparatus executing the detection algorithm and managing all other blocks. Once all required conditions (belt closed, detected person, correct insertion direction), it is this component that will analyze the data from the inertial module in order to define the time to trigger the airbag.

Figure 3:
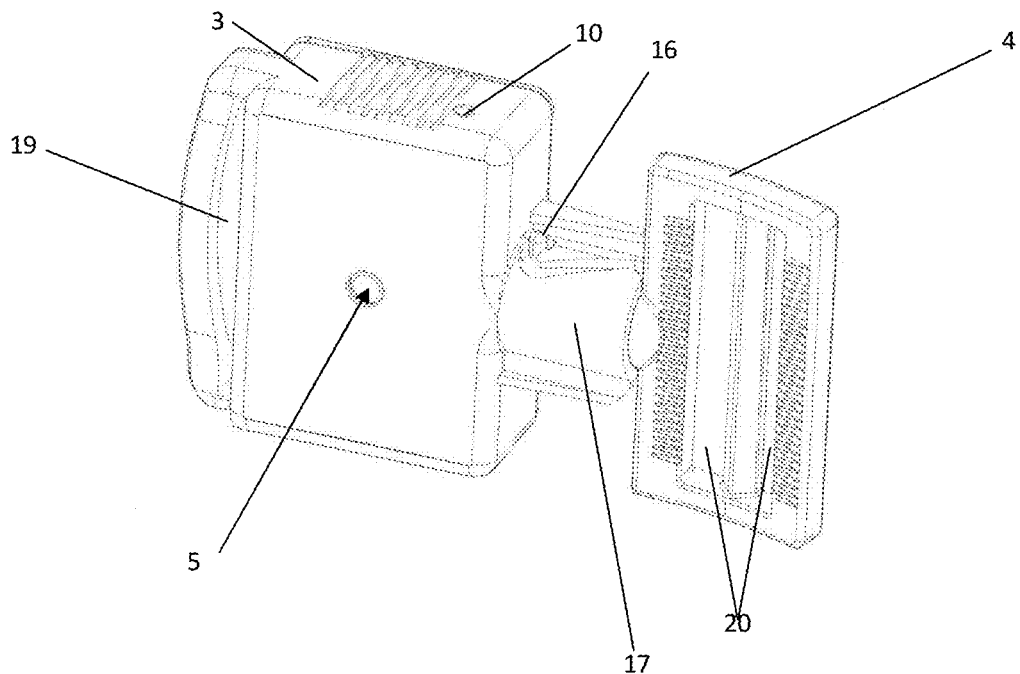
FIG. 3 is a perspective bottom view of the buckle of the airbag safety device.
Figure 4:
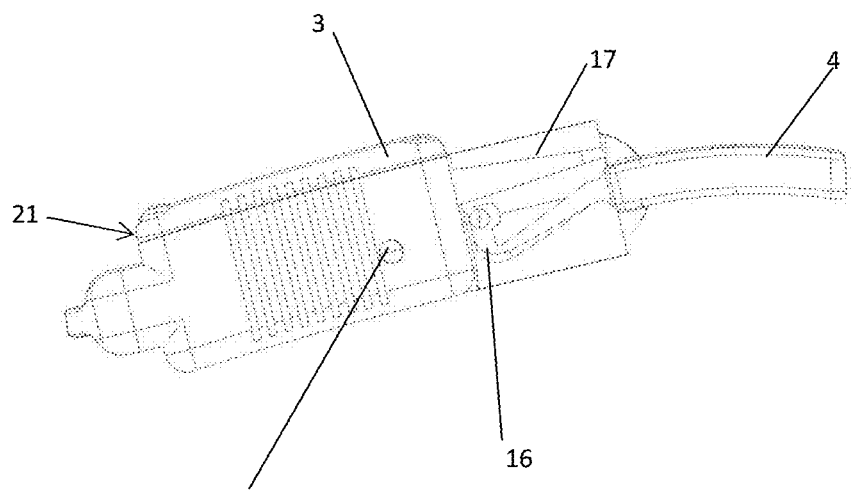
FIG. 4 is a side view of the buckle of the airbag safety device.

One of the sensors which are arranged in the portion 3 of the buckle is a thermal sensor 5 (FIG. 3) arranged on the inner side of this portion 3 in order to measure the body temperature of the wearer 6 coupled with an ambient temperature sensor arranged inside the housing of the buckle, and therefore not visible in the drawing, to provide a signal to enable triggering of the airbag in case of a fall only when the device is worn by a wearer 6. The thermal sensor 5 is an infrared thermometer for measuring the temperature of a distant body in particular detecting the human heat of the wearer 6. Coupled with the measurement of the ambient temperature, the system indicates whether the belt is properly worn by a person rather than simply stored in the closed position.

Figure 5:
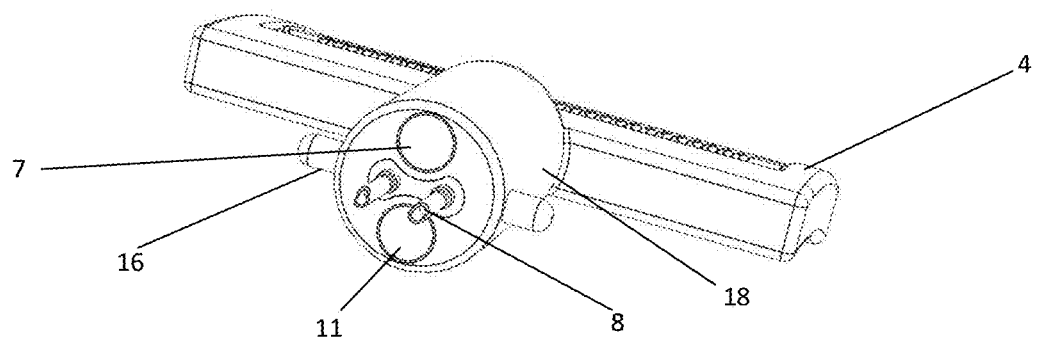
FIG. 5 is a perspective view of a portion of the buckle of the airbag safety device.

As illustrated in FIG. 5, the inner end of the portion 4 of the buckle includes two magnets 7, 11 for locking the buckle and a spring-loaded piston contact 8 for activating the device, once the belt is closed. The electronics allows managing the switching on of the device. Spring-loaded piston contacts 8 on each buckle portion make contact on each buckle portion to detect that the buckle of the belt is closed.

Figure 6:
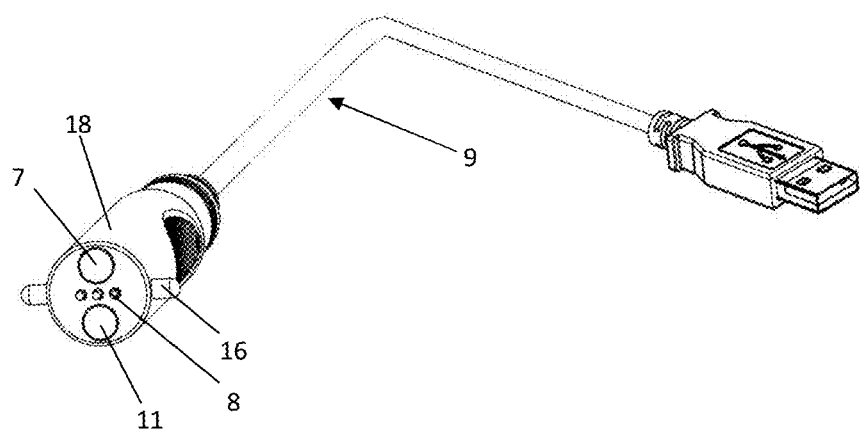
FIG. 6 is a perspective view of another portion of the airbag safety device.

FIG. 6 illustrates a rechargeable energy source through the buckle portion 3, in particular by a USB cable 9. This allows an internal battery to be charged. This block can be simplified and a simple battery charger will be present.

The device according to the invention typically includes six-axis inertial module for detecting the movements of a user, the inertial module including in particular an accelerometer coupled to a gyroscope. These elements are contained in the portion 3 of the buckle. This module allows detecting, in a known manner, the movements of the person and thus predicting the fall before the impact. The accelerometer coupled to the gyroscope allows differentiating a real fall from simple vibration or normal movements of the person.

The portion 3 of the buckle includes an opening 21 (FIG. 1) in the side thereof, which is arranged to pass an electric wire 12 disposed to transmit an electrical pulse given by the microcontroller to enable triggering of the airbag in case of a fall.

Figure 2:
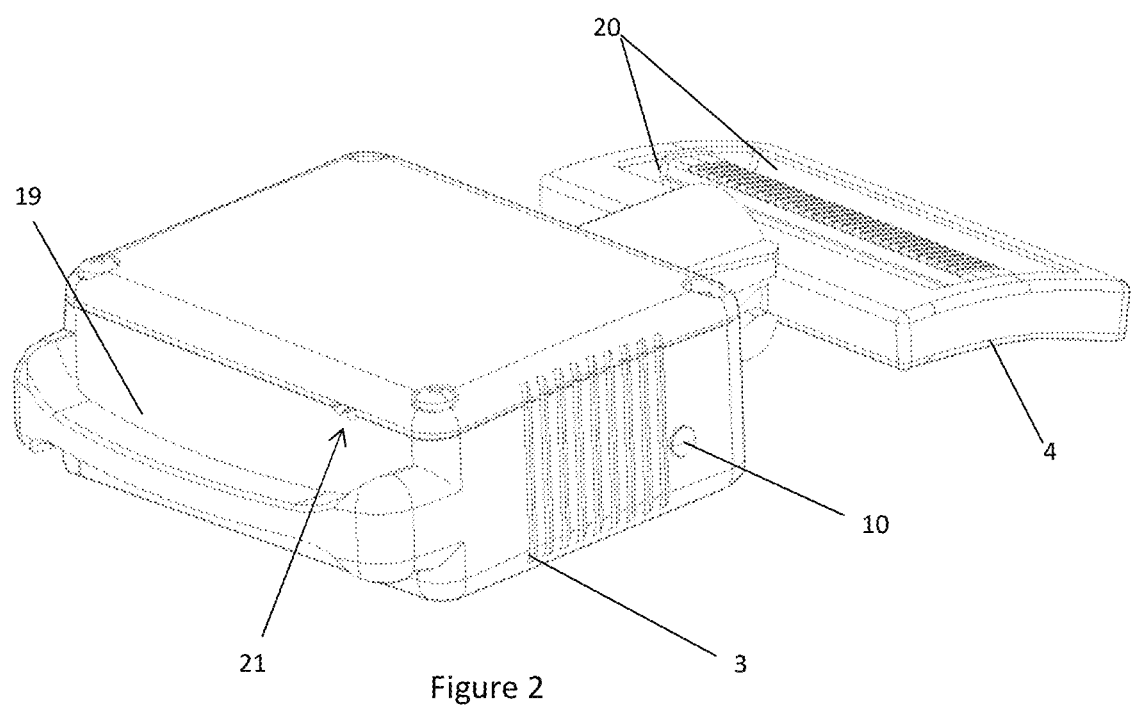
FIG. 2 is a perspective top view of a buckle of the airbag safety device.

In this example, a LED 10 (FIG. 2) and a buzzer, which is not illustrated, for informing the wearer of the operating state of the device, in particular by emitting a flashing of the LED 10 in case of a malfunction and then the emission of several beeps if the wearer has not reacted to the signals emitted by the LED 10.

The device can optionally include an auditory or light device for indicating to the user other situations than a malfunction. For example: when the activated belt is worn correctly: two high-pitched beeps; when the belt is worn but upside down: two low-pitched beeps; when the belt is removed, switching off of the device: low-pitched beep; low battery: four quick low-pitched beeps every fifteen minutes.

As illustrated, the buckle is formed of two assemblable portions, a first portion 3 in the form of a rectangular housing containing electronics (in particular the sensors as well as the microcontroller), and a second recessed rectangular portion 4. These two portions 3, 4 together include a cylindrical connection body 15 including a bayonet fastening device 16, i.e. a hollow cylindrical portion 17 on one side of the portion 3 which receives a solid cylindrical portion 18 on one side of the portion 4. The main surfaces of the portions 3, 4 are flat, which is the case for the portion 3, or slightly curved, which is the case for the portion 4, in order to be able to be urged to press against the body of the wearer 6. The outer sides of the portions 3 and 4 include elongated openings 19, 20 to be attached to the ends of the bag 1 forming a belt.

Figure 7:
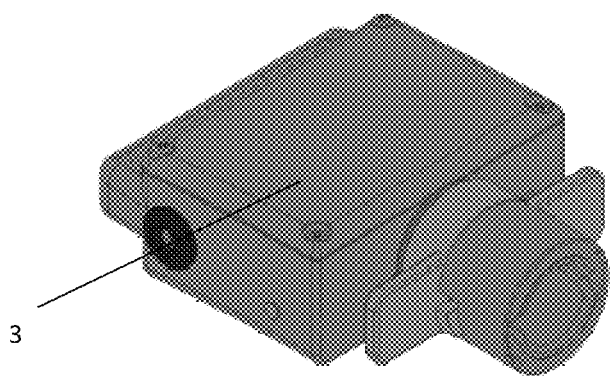
FIGS. 7 and 8 are perspective views of another version of the buckle of the airbag safety device.
Figure 8:
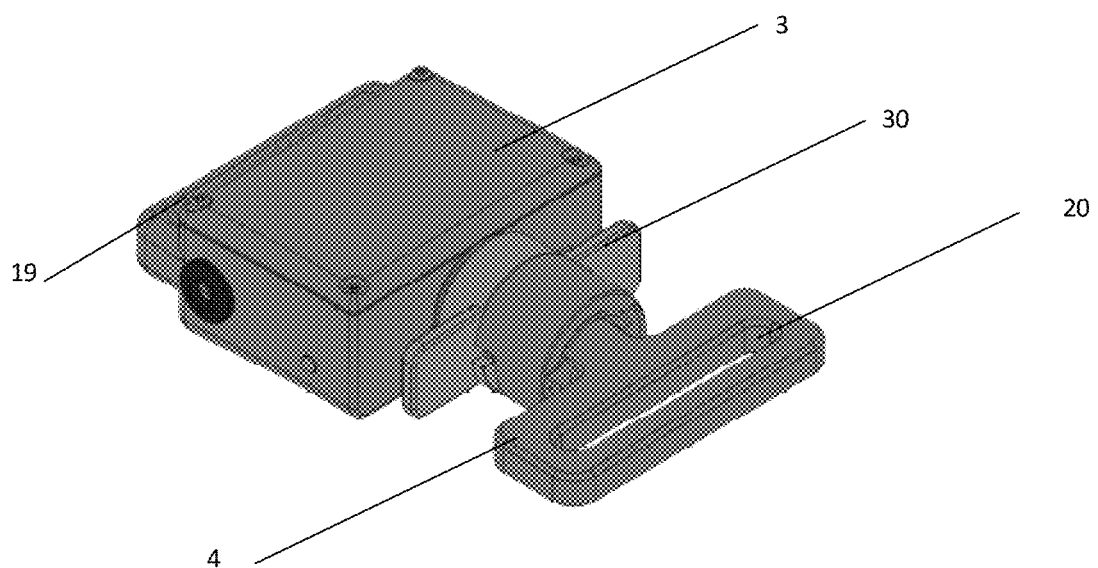

As illustrated in FIGS. 7 and 8, the buckle is formed of two assemblable portions, a first portion 3 in the form of a rectangular housing containing electronics and a second recessed rectangular portion 4. These two portions 3, 4 together include a cylindrical connection body including a fastening device including two projections 30 facilitating the opening of the buckle. The outer sides of the portions 3 and 4 include elongated openings 19, 20 to be attached to the ends of the bag forming a belt.

What is claimed is:

1. A safety device adapted to be worn by a wearer (6) for preventing injuries to the hips, the pelvis, the buttocks and the coccyx of the wearer (6) by airbag inflation, said device comprising:
   a portable inflatable bag (1);
   at least one source (2) of releasable gas coupled to the inflatable bag (1);
   a belt buckle (3, 4) in which a plurality of sensors are arranged, for determining the angular movement and the acceleration of the wearer (6) of the safety device during a fall of the wearer;
   a microcontroller adapted to analyze data received by different functional blocks in order to define a time to trigger the gas source; and
   means for causing the source (2) of releasable gas to release the gas into the bag (1) according to a determination by the microcontroller that the wearer is falling;
   characterized in that:
   two of the sensors arranged in the belt buckle are a first thermal sensor measuring the ambient temperature and a second thermal sensor (5) measuring the body temperature of the wearer (6), the first and second thermal sensors being arranged for a deployment of the airbag in case of a fall only when the device is worn by the wearer, by measuring a temperature difference, as measured using the two thermal sensors, thus ensuring the presence of the wearer of the device and in that the device further comprises a wireless communication module, for transmitting information relating to: a state of the device corresponding to the presence or absence of the wearer; and to the deployment or non-deployment of the airbag to a person other than the wearer of said device, said means for causing the source of releasable gas to release the gas into the bag comprising an opening in said buckle, arranged to pass an electric wire (12) disposed to transmit an electrical pulse given by the microcontroller for said deployment of the airbag in case of a fall.

2. The device according to claim 1, wherein the buckle (3, 4) includes at least one magnet (7, 11) for locking the buckle.

3. The device according to claim 1, including a piston contact for activating the device, once the belt is closed.

4. The device according to claim 1, including a rechargeable energy source through the buckle (3), in particular by a USB cable (9).

5. The device according to claim 1, including a six-axis inertial module for detecting the movements of the wearer (6), the inertial module including in particular an accelerometer coupled to a gyroscope.

6. The device according to claim 1, wherein the buckle is formed of two assemblable portions, a first portion (3) in the form of a rectangular housing containing electronics and a second portion (4), these two portions together including a cylindrical connection body (15) including a bayonet fastening device (16).

7. The device according to claim 6, wherein the outer sides of said portions (3, 4) Include openings (19, 20) to be attached to the ends of the bag (1) forming a belt.

8. The device according to claim 1, including visual and/or sound means arranged to indicate the operating state of said device.

9. The device according to claim 1, including a buckle comprising:
   a first cylindrically shaped portion including a helical groove extending from one end of the first buckle portion, the groove being curved with a notch at the second end thereof, and
   a second portion including a protrusion arranged to slide in said groove and be engaged into said notch,
      each portion of the buckle including a magnet arranged to hold together the first and second buckle portions, the two said buckle portions being disengageable from each other by the angular displacement of a first buckle portion relative to the other buckle portion then by the sliding of the protrusion in the groove until the extraction thereof.

10. The device according to claim 1, wherein the microcontroller stores an algorithm which distinguishes between sudden movements which correspond to falls and other movements which do not correspond to falls, in order to define the time to trigger the gas source only in case of a fall.

* * * * *